(12) United States Patent
Matsuura et al.

(10) Patent No.: US 8,466,310 B2
(45) Date of Patent: Jun. 18, 2013

(54) PROCESS FOR PRODUCING α-SUBSTITUTED NORBORNANYL ACRYLATES

(75) Inventors: Makoto Matsuura, Kawagoe (JP); Ryo Nadano, Kawagoe (JP); Takeo Komata, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 328 days.

(21) Appl. No.: 13/058,115

(22) PCT Filed: Aug. 27, 2009

(86) PCT No.: PCT/JP2009/064973
§ 371 (c)(1),
(2), (4) Date: Feb. 8, 2011

(87) PCT Pub. No.: WO2010/024339
PCT Pub. Date: Mar. 4, 2010

(65) Prior Publication Data
US 2011/0137073 A1 Jun. 9, 2011

(30) Foreign Application Priority Data

| Sep. 1, 2008 | (JP) | 2008-223942 |
| Aug. 3, 2009 | (JP) | 2009-181131 |
| Aug. 26, 2009 | (JP) | 2009-195145 |

(51) Int. Cl.
*C07C 67/04* (2006.01)
*C07C 69/54* (2006.01)
*C07B 61/00* (2006.01)

(52) U.S. Cl.
USPC ............................................. 560/220

(58) Field of Classification Search
None
See application file for complete search history.

(56) References Cited

U.S. PATENT DOCUMENTS

| 6,784,312 B2 | 8/2004 | Miyazawa et al. |
| 6,833,462 B2 | 12/2004 | Ishikawa et al. |
| 7,148,363 B2 | 12/2006 | Ishikawa et al. |
| 2003/0078352 A1 | 4/2003 | Miyazawa et al. |
| 2003/0139613 A1 | 7/2003 | Ishikawa et al. |
| 2005/0148789 A1 | 7/2005 | Ishikawa et al. |

FOREIGN PATENT DOCUMENTS

| JP | 59-21648 A | 2/1984 |
| JP | 4-13647 A | 1/1992 |
| JP | 8-134015 A | 5/1996 |
| JP | 2003-40840 A | 2/2003 |
| JP | 2003-226670 A | 8/2003 |
| JP | 2004-175740 A | 6/2004 |
| JP | 2005-179348 A | 7/2005 |
| JP | 2006-137727 A | 6/2006 |
| KR | 2003-0043776 A | 6/2003 |

OTHER PUBLICATIONS

Shin Jikken Kagaku Koza,(vol. 14) Synthesis and Reactions of Organic Compounds [II], pp. 1017-1021, edited by The Chemical Society of Japan and published by Maruzen Co., Ltd., Dec. 1977.
Chiba et al., 157 nm Resist Materials: A Progress Report, Journal of Photopolymer Science and Technology, 2000, pp. 657-664, vol. 13, No. 4.
International Search Report with partial English translation dated Oct. 27, 2009 (three (3) pages).
Form PCT/ISA/237 dated Oct. 27, 2009 (three (3) pages).
Korean Office Action dated Oct. 12, 2012 (eleven (11) pages).

*Primary Examiner* — Yevegeny Valenrod
(74) *Attorney, Agent, or Firm* — Crowell & Moring LLP

(57) ABSTRACT

Disclosed is a process for producing α-substituted norbornanyl acrylates efficiently on an industrial scale while suppressing the formation of by-products derived from intramolecular cyclization, excessive addition to acrylic acid etc. The α-substituted norbornanyl acrylates are useful as norbornene resist monomers. In the disclosed process, an α-substituted acrylic acid is directly reacted with a substituted norbornene in the presence of at least one acid catalyst selected from methanesulfonic acid and camphorsulfonic acid. It is possible in this reaction to suppress the formation of the by-products derived from intramolecular cyclication, excessive addition of the acid to the reaction product etc.

6 Claims, No Drawings

PROCESS FOR PRODUCING α-SUBSTITUTED NORBORNANYL ACRYLATES

TECHNICAL FIELD

The present invention relates to a process for producing norbornanyl esters of the general formula [3], which are useful compound as photoresist monomers.

[Chem.1]

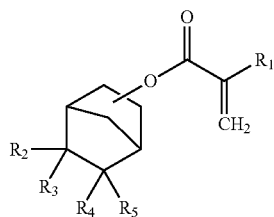

[3]

(Hereinafter, the norbornanyl esters of the general formula [3] are also referred to as "NB resist monomers".)

BACKGROUND ART

In view of the properties of fluorine, such as low refractive index and transparency, fluorine-containing compounds are useful in the field of resist technologies. Among others, hexafluorohydroxyisopropyl unit-containing compounds not only show high transparency at each wavelength because of their high fluorine content but also work effectively for improvement of hydrophilicity and adhesion due to the coexistence of a polar hydroxyl group in their compound structure (see Patent Document 1).

Norbornanyl esters of the general formula [3], which are the target compound of the present invention, are α-substituted acrylic esters each having a norbornanyl group with a hexafluorohydroxyisopropyl unit-containing carbon chain and are useful as resist monomers.

In general, the α-substituted acrylic esters can be synthesized by the following ester synthesis processes: (A) reaction of a carboxylic halide and an alcohol; (B) reaction of a carboxylic acid anhydride and an alcohol; (C) dehydration condensation reaction of a carboxylic acid and an alcohol; and (D) transesterification reaction of a carboxylic acid ester and an alcohol.

For example, Non-Patent Document 1 discloses a process of synthesizing cyclohexyl acrylate by transesterification reaction of methyl acrylate and cyclohexanol. Patent Document 1 discloses a process of synthesizing a norbornanyl ester by reaction of a norbornanyl alcohol and an α-substituted acrylic chloride.

Each of these processes is characterized in that the alcohol is used as the reaction substrate. In order to apply these processes for synthesis of the target compound of the present invention, it is necessary to first convert a norbornene of the general formula [1] to a norbornanyl alcohol of the general formula [4] by a hydroboration technique, an ester addition-ester hydrolysis technique etc., and then, react the norbornanyl alcohol with an acrylic acid, acrylic halide, acrylic anhydride or acrylic ester of the general formula [2'] as indicated in Scheme 1. Moreover, the norbornanyl alcohol intermediate (the general formula [4]) has a high viscosity and thus raises a problem in process operation. (The definitions of $R_1$ to $R_5$ in the general formula [3] of Scheme 1 will be described later; and the definitions of $R_1$ to $R_5$ in the general formulas [1], [2'] and [4] are the same as those in the general formula [3].)

Scheme 1

[Chem. 2]

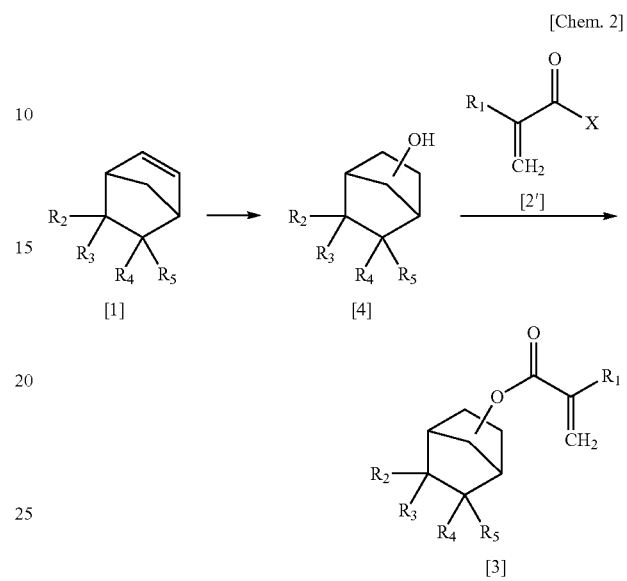

In contrast to these processes, Patent Document 2 and Patent Document 3 each disclose a process of reacting a norbornene with (meth)acrylic acid in the presence of an acid catalyst.

Further, Patent Document 4 discloses a process of reacting a substituted norbornene with an α-substituted acrylic acid in the presence of a specific acid catalyst so as to allow addition of the acid to an olefin moiety of the norbornene and thereby form a corresponding ester compound. It is also reported that p-toluenesulfonic acid, trifluoroacetic acid and trifluoromethanesulfonic acid are particularly suitable as the acid catalyst.

In Patent Document 4, the target norbornanyl ester can be obtained with less number of process steps and without going through the high-viscosity norbornanyl alcohol intermediate. The process of Patent Document 4 can be thus regarded industrially superior to the processes that proceed through the norbornanyl alcohol intermediate even though there occurs formation of by-products in this process.

PRIOR ART DOCUMENTS

Patent Documents

Patent Document 1: Japanese Laid-Open Patent Publication No. 2003-040840
Patent Document 2: Japanese Laid-Open Patent Publication No. 08-134015
Patent Document 3: Japanese Laid-Open Patent Publication No. 04-013647
Patent Document 4: Japanese Laid-Open Patent Publication No. 2004-175740

Non-Patent Documents

Non-Patent Document 1, "Shin Jikken Kagaku Koza (Vol. 14), Synthesis and Reactions of Organic Compounds [II]", edited by The Chemical Society of Japan and published by Maruzen Co., Ltd., December, 1977, P. 1018

DISCLOSURE OF THE INVENTION

It has been attempted to apply the above processes to the reaction between a norbornene compound having as a substituent group a carbon chain with a hexafluorohydroxyisopropyl unit and an α-substituted acrylic acid and has been shown that such attempts can result in problems that: the conversion rate of the reaction becomes low; and the reaction proceeds, but does not always proceed selectively, depending on the structure of the reaction substrate and the kind of the acid product.

Even the industrially superior process of Patent Document 4 causes intramolecular addition reaction between an olefin moiety and an alcohol moiety of the norbornene compound so as to form a compound having a cyclized structure in its molecule as a by-product (hereinafter referred to as "cyclization product") and show significant deterioration in yield, depending on the kind of the acid catalyst, in view of the fact that the raw norbornene compound has a side carbon chain with a hexafluorohydroxyisopropyl unit as a substituent group. For example, the following cyclization product is formed as the by-product when 5-(1,1,1-trifluoro-2-hydroxyl-2-trifluoromethyl-propyl)-norbornene is used as the norbornene compound of the formula [1].

[Chem. 3]

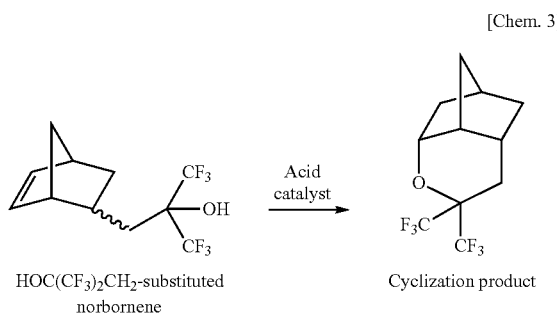

HOC(CF$_3$)$_2$CH$_2$-substituted norbornene → Cyclization product

It has further been shown that, in the addition reaction of the α-substituted acrylic acid, there also occurs a by-product in which another α-substituted acrylic acid molecule is added to a vinyl moiety of the target α-substituted acrylate compound (hereinafter referred to as "excessive addition product") depending on the kind of the acid catalyst. This phenomenon is particularly pronounced when R$_1$ is hydrogen in the acrylic acid.

[Chem. 4]

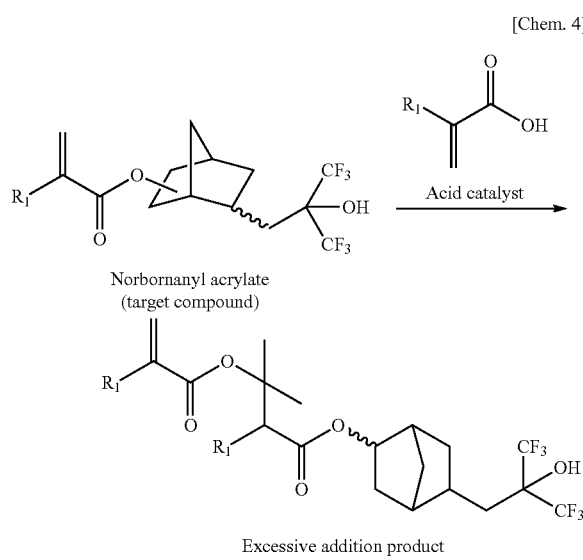

Norbornanyl acrylate (target compound)

Excessive addition product

As a result of further reaches on the by-product formation reaction, it has been shown that: the formation of the cyclization product occurs in the presence of an acid so that the presence of the acid catalyst allows formation of the cyclization product even in the absence of the α-substituted acrylic acid; and the formation of the cyclization product is more likely to occur as the acidity of the acid increases. It is thus desirable to use the acid catalyst of as low an acidity as possible in order to limit the formation of the cyclization product.

On the other hand, the target reaction proceeds even in the absence of the acid catalyst in view of the fact that the α-substituted acrylic acid itself serves as an acid catalyst. In the absence of the acid catalyst, the reaction is more likely to proceed as the acidity of the α-substituted acrylic acid increases. For example, trifluoromethyl acrylic acid (with a pKa of about 2.3) has a higher acidity and undergoes the target reaction much more favorably than acrylic acid (with a pKa of about 4.25) and methacrylic acid (with a pKa of about 4.25).

It is disclosed in Example 1 of Patent Document 4 that the formation of the cyclization product can suitably be limited about 22% by the combined use of trifluoromethyl acrylic acid (hereinafter also referred to as "TFMA") and p-toluenesulfonic acid monohydrate. It is also disclosed in Example 3 of Patent Document 4 that the formation of the cyclization product reaches 35% and thus cannot be limited sufficiently by the combined use of acrylic acid and p-toluenesulfonic acid monohydrate. Namely, even when the same acid catalyst is used, the formation amount of the by-product significantly increases with decrease in the acidity of the α-substituted acrylic acid. It is thus necessary to select and use the acid catalyst so as to limit the formation of the by-product even when the acidity of the α-substituted acrylic acid used is not so high.

In the synthesis processes of the prior art documents, the above side reaction problems and solutions thereto are not specifically indicated or suggested. There has been a demand for a process of producing an α-substituted norbornanyl acrylate efficiently on an industrial scale from an α-substituted acrylic acid while preventing by-products derived from intramolecular addition and excessive addition to the acrylic acid even in the case where the acidity of the α-substituted acrylic acid used is not so high. It is accordingly an object of the present invention to provide such a production process of the α-substituted norbornanyl acrylate.

In view of the above prior art problems, the present inventors have made extensive researches on various kinds of acid catalysts in order to establish a suitable process for industrial-scale production of a NB resist monomer having as a substituent group a carbon chain with a hexafluorohydroxyisopropyl unit and, as a result, have found that the direct reaction of a substituted norbornene of the general formula [1] and an α-substituted acrylic acid of the general formula [2] in the presence of a specific acid catalyst makes it possible to limit the occurrence of side reactions and allow efficient addition of the acid to the norbornene so that a target norbornene resist monomer of the general formula [3] can be obtained with high yield. The present invention is based on this finding.

The process of the present invention is summarized in Scheme 2. (The definitions of R$_1$ to R$_5$ in the general formula

[3] of Scheme 2 will be described later; and the definitions of $R_1$ to $R_5$ in the general formulas [1] and [2] are the same as those in the general formula [3].)

Scheme 2

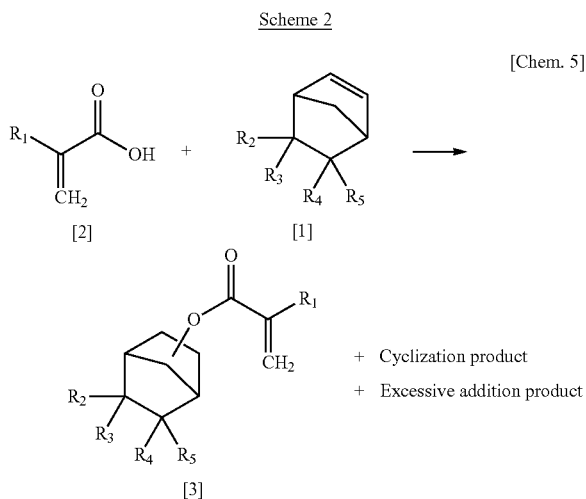

Namely, there is provided according to the present invention a process (first process) for producing an α-substituted norbornanyl acrylate of the general formula [3], comprising: conducting addition reaction of an α-substituted acrylic acid of the general formula [2] to a substituted norbornene of the general formula [1] in the presence of an acid catalyst, wherein the acid catalyst is one or more selected from the group consisting of methanesulfonic acid and camphorsulfonic acid.

[Chem. 6]

[Chem. 7]

[Chem. 8]

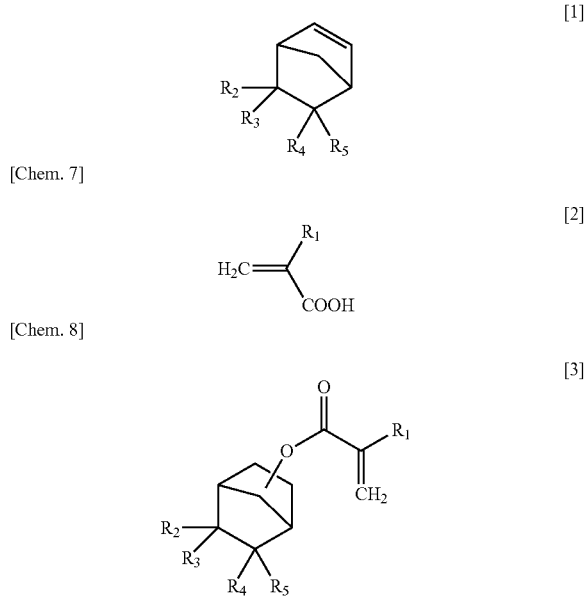

In the general formulas [1] and [3], $R_2$ to $R_5$ each independently represent a substituent group selected from a hydrogen atom, a hydroxyl group, a carboxyl group, a thiol group, thiocarbonyl group, an amino group and a $C_1$-$C_8$ lower alkyl group (in which part or all of hydrogen atoms may be substituted with a fluorine atom and/or a hydroxyl group); and at least one of the substituent groups $R_2$ to $R_5$ has a carbon chain with a hexafluorohydroxyisopropyl unit represented by HOC$(CF_3)_2(CH_2)_n$— (where n is an integer of 0 to 5). Further, $R_1$ represents a substituent group selected from a hydrogen atom and a $C_1$-$C_6$ lower alkyl group.

The first process may be the process (second process) for producing the α-substituted norbornanyl acrylate, in which any of the substituent groups, other than the substituent group having the carbon chain with the hexafluorohydroxyisopropyl unit by HOC$(CF_3)_2(CH_2)_n$— (where n is the integer of 0 to 5), is a hydrogen atom.

The first or second process may be the process (third process) for producing the α-substituted norbornanyl acrylate, in which the substituent group $R_1$ is a hydrogen atom or a methyl group in the general formulas [2] and [3].

Either of the first to third processes may be the process (fourth process) for producing the α-substituted norbornanyl acrylate, in which: the substituent group $R_1$ is a hydrogen atom in the general formulas [2] and [3]; and the acid catalyst is camphorsulfonic acid.

Either of the first to third processes may be the process (fifth process) for producing the α-substituted norbornanyl acrylate, in which: the substituent group $R_1$ is a methyl group in the general formulas [2] and [3]; and wherein the acid catalyst is methanesulfonic acid.

Either one of the first to fifth processes may be the process (sixth process) for producing the α-substituted norbornanyl acrylate, in which the addition reaction of the acid is conducted at a reaction temperature of 30 to 200° C.

DETAILED DESCRIPTION

It is possible by the process of the present invention to limit the formation of by-products in the reaction of the substituted norbornene and the α-substituted acrylic acid, even when the α-substituted acrylic acid is not high in acidity, so that the target norbornene resist monomer can be obtained with high yield. The process of the present invention is thus particularly superior for the industrial-scale production of the norbornene resist monomer.

Hereinafter, the present invention will be described in detail below. The process of the present invention can be carried out by means of a batch-type reactor. Although the reaction conditions of the reactor will described below in detail, it should be appreciated that a person skilled in the art can easily modify and/or improve the reaction conditions of the reactor.

The substituent group $R_1$ of the α-substituted acrylic acid of the general formula [2], used as the raw material of the present invention, is a hydrogen atom, a halogen atom or a $C_1$-$C_6$ lower alkyl group. Specific examples of $R_1$ are hydrogen, methyl, ethyl, n-propyl, iso-propyl, n-butyl, iso-butyl, t-butyl and the like. Among others, $R_t$ is preferably hydrogen or methyl. The α-substituted carboxylic acid with such a substituent group is a weaker acid than trifluoromethyl carboxylic acid and is not itself so high in reactivity.

The α-substituted acrylic acid can be prepared by a known process. Further, the α-substituted acrylic acid in which $R_1$ is hydrogen or methyl is also readily available as a reagent. For example, it is known that the α-substituted acrylic acid in which $R_1$ is trifluoromethyl can be easily prepared by CO insertion reaction (Heck reaction) of 2-bromo-1,1,1-trifluoropropene with the use of Pd as a catalyst (see Japanese Laid-Open Patent Publication No. 59-21648).

The substituent groups $R_2$, $R_3$, $R_4$ and $R_5$ of the substituted norbornene of the general formula [1], used as the raw material of the present invention, are each independently a hydrogen atom, a hydroxyl group, a carboxyl group, a thiol group, a thiocarbonyl group, an amino group or a $C_1$-$C_8$ lower alkyl group (in which part or all of hydrogen atoms may be substituted with a fluorine atom and/or a hydroxyl group). At least one of the substituent groups $R_2$, $R_3$, $R_4$ and $R_5$ has a carbon chain with a hexafluorohydroxyisopropyl unit represented by $HOC(CF_3)_2(CH_2)_n$— (where n is an integer of 0 to 5).

Specific examples of $R_2$, $R_3$, $R_4$ and $R_5$ are: hydrogen; hydroxyl; carboxyl; thiol; thiocarbonyl; amino such as $H_2N$—, $(CH_3)_2N$—, $(C_2H_5)_2N$— and the like; $C_1$-$C_8$ lower alkyl groups in which part or all of hydrogen atoms may be substituted with a fluorine atom and/or a hydroxyl group, such as methyl, ethyl, $CF_3$—, $C_2F_5$—, $CF_3CH_2$—, $CF_3(CF_3)CH$—, $(HO)CH_2$—, $(HO)CH_2CH_2$—, $CF_3CH(OH)CH_2$—, $CF_3C(CF_3)(OH)CH_2$—, $HOC(CF_3)_2(CH_2)_2$— and the like. The substituent groups $R_2$, $R_3$, $R_4$ and $R_5$ are not however limited to the above. At least one of the substituent groups $R_2$, $R_3$, $R_4$ and $R_5$ has a carbon chain with a hexafluorohydroxyisopropyl unit represented by $HOC(CF_3)_2(CH_2)_n$— (n=0 to 5), such as $HOC(CF_3)_2CH_2$—, $HOC(CF_3)_2(CH_2)_2$— or the like, as mentioned above.

As a preferred example of the substituted norbornene, there can be used 5-(1,1,1-trifluoro-2-hydroxyl-2-trifluoromethyl-propyl)-norbornene compound (as represented by the general formula [5]) having a hydroxyl group as $R_2$, $R_3$ and $R_4$ and $CF_3C(CF_3)(OH)CH_2$— group as $R_5$.

[Chem. 9]

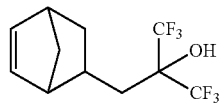

[5]

It is known that the substituted norbornene raw material of the general formula [1] can be prepared by Diels Alder reaction of a corresponding olefin and cyclopentadiene in the presence or absence of a Lewis acid catalyst.

For example, it is reported that the above 5-(1,1,1-trifluoro-2-hydroxyl-2-trifluoromethyl-propyl)-norbornene compound in which $R_2$, $R_3$ and $R_4$ are hydroxyl and $R_5$ is $CF_3C(CF_3)(OH)CH_2$— can be obtained with a yield of 33% by reaction of 1,1,1-trifluoro-2-(trifluoromethyl)penta-4-ene-2-ol and cyclopentadiene (see J. Photopolym. Sci. Technol., Vol. 13, No. 4, 2000, P. 657). The 1,1,1-trifluoro-2-(trifluoromethyl)penta-4-ene-2-ol used as the reaction substrate in this reaction can be prepared by e.g. reaction of an allyl Grignard reagent and hexafluoroacetone (see J. Photopolym. Sci. Technol., Vol. 13, No. 4, 2000, P. 657).

In the present invention, it is preferable to conduct the reaction in the coexistence of a specific acid catalyst in order to promote the reaction efficiently. However, there occur by-products of the reaction depending on the kind of the acid catalyst and the structure of the substrate material. It is thus necessary to pay particular attention to the selection of the acid catalyst.

As already mentioned above, there are two main by-products; one of which is a cyclization product resulting from the intramolecular addition reaction between an olefin moiety of the norbornene and an alcohol moiety of the hexafluorohydroxyisopropyl unit of the substituent group of the norbornene and the other of which is a product of addition of another acrylic acid molecule to a vinyl moiety of the target acrylate compound. For example, a cyclization product of the formula [6] and an excessive addition product of the formula [7] are formed when 5-(1,1,1-trifluoro-2-hydroxyl-2-trifluoromethyl-propyl)-norbornene (the above formula [5]) is used as the raw material.

[Chem. 10]

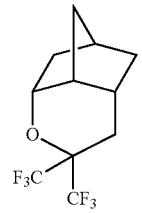

[6]

Cyclization product

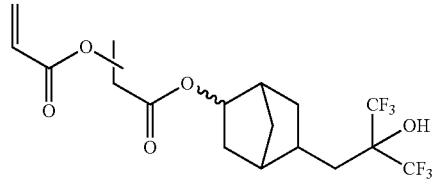

[7]

Excessive addition product

In order to prevent these by-products and promote the reaction efficiently, at least one acid selected from the group consisting of methanesulfonic acid and camphorsulfonic acid is suitably used as the acid catalyst. It is herein known that the camphorsulfonic acid has a sterically bulky structure as indicated below.

[Chem. 11]

In general, it is preferable to use the camphorsulfonic acid when the substituent group $R_1$ of the α-substituted acrylic acid of the general formula [2] is hydrogen and to use the methanesulfonic acid when the substituent group $R_1$ of the α-substituted acrylic acid of the general formula [2] is methyl.

As the effect of the acid catalyst varies depending on the combination of the substituted norbornene, α-substituted acrylic acid, solvent and acid, the amount of the acid catalyst used in the reaction cannot be uniquely defined. The amount of the acid catalyst used is generally 0.0001 to 1 mol, preferably 0.005 to 0.5 mol, more preferably 0.01 to 0.2 mol, per 1 mole of the substituted norbornene substrate. It is undesirable to use the acid catalyst in an amount of less than 0.0001 mol per 1 mole of the substituted norbornene substrate as there is no effect obtained by the use of such a small amount of the acid catalyst. It is economically undesirable to use the acid catalyst in an amount exceeding 1 mol per 1 mole of the substituted norbornene substrate.

There is no particular limitation on the mixing ratio of the α-substituted acrylic acid and the substituted norbornene. The amount of the α-substituted acrylic acid is generally 0.1 to 20 mol, preferably 0.5 to 5 mol, more preferably 1 to 3 mol, per 1 mol of the substituted norbornene. It is undesirable to use the α-substituted acrylic acid in an amount of less than 0.1 mol per 1 mole of the substituted norbornene as the use of such a small amount of the α-substituted acrylic acid leads to decreases of both of the selectivity of the reaction and the yield of the target compound. It is economically undesirable to use the α-substituted acrylic acid in an amount exceeding 20 mol per 1 mole of the substituted norbornene.

Although the reaction proceeds even in the absence of the solvent, the solvent can be used in order to prevent the side reactions and carry out the target reaction smoothly. As the solvent, it is preferable to use at least one kind selected from the group consisting of: nitrile solvents such as acetonitrile, benzonitrile and the like; amide solvents such as N,N-dimethylformamide, N,N-dimethylacetoamide, N,N-dimethylimidazolidinone and the like; sulfoxide solvents such as dimethyl sulfoxide and the like; ether solvents such as diethyl ether, diisopropyl ether, dibutyl ether and the like; halogenated solvents such as methylene chloride, chloroform, carbon tetrachloride and the like; aromatic hydrocarbon solvents such as benzene, toluene, xylene and the like; and aliphatic hydrocarbon solvents such as pentane, hexane, heptane and the like. The above solvent compounds can be used solely or in combination of two or more thereof.

In the case of using the solvent, the amount of the solvent used is generally 0.01 to 100 g, preferably 1 to 30 g, more preferably 2 to 10 g, per 1 g of the substituted norbornene. It is economically undesirable to use the solvent in an amount exceeding 100 g per 1 g of the substituted norbornene in view of the expense in time and effort of the post treatment and solvent recovery etc.

In the present invention, the temperature of the reaction is in the range of 30 to 200° C., preferably 50 to 150° C., more preferably 80 to 130° C. If the reaction temperature is lower than 30° C., the rate of the reaction becomes too low to make the process practical. There undesirably occurs polymerization of the substituted acrylic acid if the reaction temperature exceeds 200° C.

Further, the reaction may be conducted in the coexistence of a polymerization inhibitor in order to prevent polymerization of the substituted acrylic acid or the norbornanyl ester product. It is preferable to use as the polymerization inhibitor at least one compound selected from the group consisting of methoquinone, 2,5-di-t-butylhydroquinone, 1,2,4-trihydroxybenzene, 2,5-bistetramethylbutylhydroquinone, leucoquinizarin, Nonflex F, Nonflex H, Nonflex DCD, Nonflex MBP, Ozonone 35, phenothiazine, tetraethylthiuram disulfide, 1,1-diphenyl-2-picrylhydrazyl, 1,1-diphenyl-2-picrylhydrazine, Q-1300 and Q-1301. The above polymerization inhibitors are commercially available and are thus easy to get.

The amount of the polymerization inhibitor used is generally 0.00001 to 0.1 mol, more preferably 0.00005 to 0.05 mol, more preferably 0.0001 to 0.01 mol, per 1 mol of the substituted norbornanyl alcohol raw material. If the amount of the polymerization inhibitor exceed 0.1 mol per 1 mol of the substituted norbornanyl alcohol raw material, there is not so large a difference in polymerization inhibition effect so that it is economically undesirable to use such a large amount f the polymerization inhibitor. It is difficult to obtain the effect of the use of the polymerization inhibitor if the amount of the polymerization inhibitor is less than 0.00001 mol per 1 mol of the substituted norbornanyl alcohol raw material.

As the reactor for the reaction of the present invention, there can preferably be used those formed with an inner liner of polytetrafluoroethylene resin, chlorotrifluoroethylene resin, vinylidene fluoride resin, PFA resin, glass etc. or those made of glass, stainless steel etc.

Although there is no particular limitation on the system in which the present invention is embodied, one preferred embodiment of the present invention will be explained below. It is preferable to, after adding the acid catalyst, the solvent and the raw materials i.e. the substituted norbornene and the substituted acrylic acid into the reactor that is capable of withstanding the reaction conditions, heat the reactor externally to promote the reaction, monitor the consumption of the raw materials by sampling etc. to confirm the completion of the reaction, and then, cool the resulting reaction solution.

The α-substituted norbornanyl acrylate of the general formula [3] produced by the process of the present invention can be purified by any known technique. For example, the α-substituted norbornanyl acrylate can be obtained as a crude organic substance by treating the reaction solution with an aqueous alkali solution, removing excessive α-substituted acrylic acid by separation operation and removing the solvent by evaporation. The norbornene resist monomer can be obtained with high purity by purification such as column chromatography or distillation of the crude organic substance.

There can suitably be used a distillation technique for purification of the target norbornene resist monomer as the target norbornene resist monomer and the by-produced cyclization product can be easily separated from each other by distillation.

When the molecular structure of the norbornene raw material is asymmetrical, the reaction product is obtained as a mixture of two isomers of the α-substituted norbornanyl acrylate of the general formula [3] as represented by the following formulas [3a] and [3b].

[Chem.12]

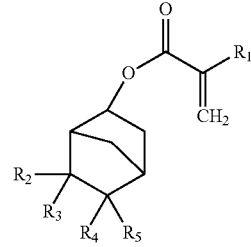

[3a]

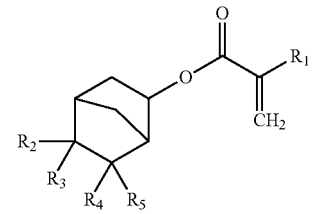

[3b]

There can be adopted a column chromatography etc. for isolation and separation of these isomers. Further, the mixture of the isomers can be used as a resist monomer without separating the isomers.

EXAMPLES

The present invention will be described in more detail below by way of the following examples. It should be noted that these examples are illustrative and are not intended to limit the present invention thereto. Herein, the unit "%" of composition analysis values represents "area %" of organic components excluding solvent components, each obtained by sampling a part of the reaction mixture, washing the sample with water sufficiently, extracting the organic component with diethyl ether from the washed sample and measuring the diethyl ether phase by gas chromatography.

Example 1

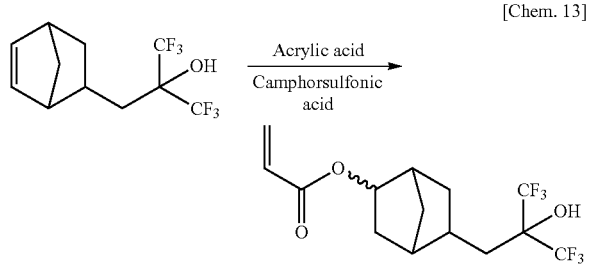

[Chem. 13]

Into a 1-L three-neck flask with a reflux condenser attached to a top portion thereof, were placed 3.0 g of camphorsulfonic acid, 86.7 g of acrylic acid and 300 g of 5-(1,1,1-trifluoro-2-hydroxyl-2-trifluoromethyl-propyl)-norbornene as raw material. The flask was then heated in an oil bath of 120° C. After a lapse of 20 hours, the composition of the resulting reaction solution was analyzed by gas chromatography. The reaction conversion rate was 98%. The total amount of the mixture of isomers of a target α-substituted norbornanyl acrylate was 72% (selectivity: 73%). There were also detected, as impurities, 19% of 5,5-bis(trifluoromethyl)-4-oxatricyclo[5.2.1.0$^{3,8}$]decane derived from intramolecular cyclization of the raw material (selectivity: 20%), 2% of the 5-(1,1,1-trifluoro-2-hydroxyl-2-trifluoromethyl-propyl)-norbornene raw material and 4% of addition compound of one acrylic acid molecule to a vinyl moiety of the acrylate product (as excessive addition product) (selectivity: 4%).

The reaction solution was cooled and then admixed with 3.0 g of sodium carbonate ($Na_2CO_3$). The resulting solution was subjected to distillation under reduced pressure (0.6 Torr=80 Pa) to collect a fraction at 100 to 120° C. With this, 258 g of the norbornene resist monomer was obtained. The composition of the norbornene resist monomer was analyzed by gas chromatography. The total selectivity of the isomer mixture of the target acrylic acid 5-(2-triluforomethyl-2-hydroxyl-1,1,1-trifluoropropyl)-norbomanyl ester and acrylic acid 6-(2-trifluoromethyl-2-hydroxyl-1,1,1-trifluoropropyl)-norbornanyl ester was 99.2%; and the selectivity of the intramolecular cyclization product was 0.2%.

Comparative Examples 1 to 5

The reaction was performed in the same manner as in Example 1, except for using p-toluenesulfonic acid, trifluoroacetic acid, trifluoromethanesulfonic acid or fluorosulfonic acid as the acid catalyst.

Into a 100-mL two-neck flask with a reflux condenser attached to a top portion thereof, were placed 0.25 g of the acid, 14.5 g of acrylic acid and 50 g of 5-(1,1,1-trifluoro-2-hydoxyl-2-trifluoromethyl-propyl)-norbornene. The flask was then heated in an oil bath of given temperature. After a lapse of a given time period, the composition of the resulting reaction solution was analyzed by gas chromatography. The reaction conditions, the reaction conversion rate and the selectivity of the target compound of each of Example 1 and Comparative Examples 1 to 5 are indicated in TABLE 1.

TABLE 1

| | Acid (Amount of addition to raw material) | Reaction temperature (° C.) | Reaction time (h) | Conversion rate (%) | Selectivity (%) |
|---|---|---|---|---|---|
| Example 1 | camphorsulfonic acid (1 wt %) | 120 | 20 | 98 | 73 |
| Comparative Example 1 | p-toluenesulfonic acid (0.5 wt %) | 120 | 20 | 32 | 47 |
| Comparative Example 2 | trifluoroacetic acid (0.5 wt %) | 120 | 20 | 14 | 36 |
| Comparative Example 3 | trifluoromethane sulfonic acid (0.5 wt %) | 80 | 20 | 97 | 33 |
| Comparative Example 4 | trifluoromethane sulfonic acid (0.5 wt %) | 30 | 20 | 90 | 42 |
| Comparative Example 5 | fluorosulfonic acid (0.5 wt %) | 120 | 20 | 93 | 48 |

| | Raw material (%) | Cyclization product (%) | Excessive addition product (%) | Others (%) | Yield (%) |
|---|---|---|---|---|---|
| Example 1 | 2 | 20 | 4 | 1 | 72 |
| Comparative Example 1 | 68 | 47 | 4 | 2 | 15 |
| Comparative Example 2 | 86 | 59 | 2 | 3 | 5 |
| Comparative Example 3 | 3 | 55 | 11 | 1 | 32 |
| Comparative Example 4 | 10 | 54 | 2 | 2 | 38 |
| Comparative Example 5 | 7 | 36 | 15 | 1 | 45 |

In Comparative Example 1 (where p-toluenesulfonic acid was used as the acid catalyst) and Comparative Example (where trifluoroacetic acid was used as the acid catalyst), the reaction conversion rate was low so that the reaction itself was less likely to occur; and the selectivity of the target compound was also low.

In Comparative Examples 3 and 4 (where trifluoromethanesulfonic acid was used as the acid catalyst), the reaction conversion rate was favorably 90% or higher; but the selectivity of the target compound was low. (For example, the selectivity of the target compound was 33%; the selectivity of the excessive addition product was 11%; and the selectivity of the cyclization product was 55% in Comparative Example 3.)

In Comparative Example 5 (where fluorosulfonic acid was used as the acid catalyst), the reaction conversion rate was favorable; but the selectivity of the target compound was low.

Example 2

Into a 1-L three-neck flask with a reflux condenser attached to a top portion thereof, were placed 3.0 g of methanesulfonic acid, 104 g of methacrylic acid and 200 g of 5-(1,1,1-trifluoro-2-hydroxyl-2-trifluoromethyl-propyl)-norbornene. The flask was then heated in an oil bath of 120° C. After a lapse of 8 hours, the composition of the resulting reaction solution was analyzed by gas chromatography. The total amount of the mixture of isomers of a target α-substituted norbornanyl acrylate was 78%. There were also detected, as impurities, 20% of 5,5-bis(trifluoromethyl)-4-oxatricyclo[5.2.1.0$^{3,8}$]decane derived from intramolecular cyclization of the raw material (as cyclization product) and 2% of the 5-(1,1,1-trifluoro-2-hydroxyl-2-trifluoromethyl-propyl)-norbornene raw material.

The reaction solution was cooled, followed by adding thereto 300 mL of 5% aqueous sodium hydroxide (NaOH) solution while cooling. The aqueous phase was removed from the resulting solution. After that, the organic phase was washed twice with 300 mL of water. Further, the solvent was removed from the washed organic phase. The organic phase was then subjected to distillation under reduced pressure (0.6 Torr=80 Pa) to collect a fraction at 100 to 120° C. With this, 255 g of the norbornene resist monomer was obtained. The composition of the norbornene resist monomer was analyzed by gas chromatography. The total selectivity of the isomer mixture of the target methacrylic acid 5-(2-triluoromethyl-2-hydroxyl-1,1,1-trifluoropropyl)-norbornanyl ester and methacrylic acid 6-(2-trifluoromethyl-2-hydroxyl-1,1,1-trifluoropropyl)-norbornanyl ester was 98.5%; and the selectivity of the intramolecular cyclization product was 0.2%.

Example 3

Into a 100-mL two-neck flask with a reflux condenser attached to a top portion thereof, were placed 1.0 g of camphorsulfonic acid, 17.2 g of methacrylic acid and 50 g of 5-(1,1,1-trifluoro-2-hydroxyl-2-trifluoromethyl-propyl)-norbornene. The flask was then heated in an oil bath of 120° C. After a lapse of 8 hours, the composition of the resulting reaction solution was analyzed by gas chromatography. The reaction conditions, the reaction conversion rate and the selectivity of the target compound of each of Examples 2 and 3 are indicated in TABLE 2.

Comparative Examples 6 to 9

The reaction was performed in the same manner as in Example 2, except for using p-toluenesulfonic acid, sulfuric acid or trifluoromethanesulfonic acid as the acid catalyst.

Into a 100-mL two-neck flask with a reflux condenser attached to a top portion thereof, were placed 0.2 g of the acid, 17.2 g of methacrylic acid and 50 g of 5-(1,1,1-trifluoro-2-hydroxyl-2-trifluoromethyl-propyl)-norbornene. The flask was then heated in an oil bath of given temperature. After a lapse of a given time period, the composition of the resulting reaction solution was analyzed by gas chromatography. The reaction conditions, the reaction conversion rate and the selectivity of the target compound of each of Comparative Examples 6 to 9 are also indicated in TABLE 1. It is herein noted that, in Comparative Example 6, the reaction was performed in the same manner as above, except for using 0.5 g of p-toluenesulfonic acid.

TABLE 2

|  | Acid (Amount of addition to raw material) | Reaction temperature (° C.) | Reaction time (h) | Conversion rate (%) | Selectivity (%) |
| --- | --- | --- | --- | --- | --- |
| Example 2 | methanesulfonic acid (1.0 wt %) | 120 | 8 | 97 | 78 |
| Example 3 | camphorsulfonic acid (2.0 wt %) | 120 | 8 | 97 | 68 |
| Comparative Example 6 | p-toluenesulfonic acid (0.5 wt %) | 120 | 24 | 70 | 69 |
| Comparative Example 7 | sulfuric acid (0.5 wt %) | 80 | 16 | 91 | 50 |
| Comparative Example 8 | trifluoromethane sulfonic acid (0.5 wt %) | 50 | 16 | 91 | 47 |
| Comparative Example 9 | trifluoromethane sulfonic acid (0.5 wt %) | 80 | 3 | 87 | 45 |

|  | Raw material (%) | Cyclization product (%) | Excessive addition product (%) | Others (%) | Yield (%) |
| --- | --- | --- | --- | --- | --- |
| Example 2 | 3 | 19 | 1 | 2 | 76 |
| Example 3 | 3 | 29 | 1 | 2 | 66 |
| Comparative Example 6 | 30 | 28 | 1 | 2 | 48 |
| Comparative Example 7 | 9 | 45 | 2 | 3 | 46 |
| Comparative Example 8 | 9 | 49 | 3 | 2 | 43 |
| Comparative Example 9 | 13 | 52 | 1 | 2 | 39 |

In Comparative Example 6 (where p-toluenesulfonic acid was used as the acid catalyst), the reaction conversion rate was lower than in the other examples so that the reaction itself was less likely to occur. In Comparative Example 7 (where sulfuric acid was used as the acid catalyst), Comparative Example 8 and Comparative Example 9 (trifluoromethanesulfonic acid was used as the acid catalyst), the reaction conversion rate was favorable; but the selectivity of the target compound was low.

INDUSTRIAL APPLICABILITY

In the production process of the present invention, there is no need for a step of converting the substituted norbornene to a corresponding alcohol. The reaction can be thus carried out in one step. Further, there does not occur a high-viscosity intermediate compound during the progress of the reaction step so that the reaction solution can be treated as a low-viscosity liquid throughout the reaction step. The production process of the present invention is therefore useful for production of the substituted norbornyl-containing α-substituted acrylic ester. The target compound of the present invention is useful as the resist monomer.

The invention claimed is:

1. A process for producing an α-substituted norbornanyl acrylate of the general formula [3], comprising: conducting addition reaction of an α-substituted acrylic acid of the general formula [2] to a substituted norbornene of the general formula [1] in the presence of an acid catalyst, wherein the acid catalyst is one or more selected from the group consisting of methanesulfonic acid and camphorsulfonic acid

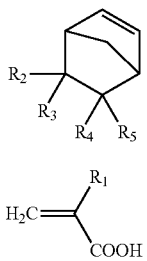

[1]

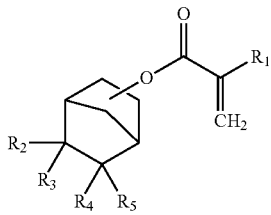

[3]

where $R_2$ to $R_5$ each independently represent a substituent group selected from a hydrogen atom, a hydroxyl group, a carboxyl group, a thiol group, thiocarbonyl group, an amino group and a $C_1$-$C_8$ lower alkyl group in which part or all of hydrogen atoms may be substituted with a fluorine atom and/or a hydroxyl group; at least one of the substituent groups $R_2$ to $R_5$ has a carbon chain with a hexafluorohydroxyisopropyl unit represented by $HOC(CF_3)_2(CH_2)_n$— (where n is an integer of 0 to 5); and $R_1$ represents a substituent group selected from a hydrogen atom or a $C_1$-$C_6$ lower alkyl group.

2. The process for producing the α-substituted norbornanyl acrylate according to claim 1, wherein any of the substituent groups $R_2$ to $R_5$, other than the said at least one of the substituent groups $R_2$ to $R_5$ having the carbon chain with the hexafluorohydroxyisopropyl unit represented by $HOC(CF_3)_2(CH_2)_n$— (where n is the integer of 0 to 5), is a hydrogen atom.

3. The process for producing the α-substituted norbornanyl acrylate according to claim 1, wherein the substituent group $R_1$ is a hydrogen atom or a methyl group in the general formulas [2] and [3].

4. The process for producing the α-substituted norbornanyl acrylate according to claim 3, wherein the substituent group $R_1$ is a hydrogen atom in the general formulas [2] and [3]; and wherein the acid catalyst is camphorsulfonic acid.

5. The process for producing the α-substituted norbornanyl acrylate according to claim 3, wherein the substituent group $R_1$ is a methyl group in the general formulas [2] and [3]; and wherein the acid catalyst is methanesulfonic acid.

6. The process for producing the α-substituted norbornanyl acrylate according to claim 1, wherein the addition reaction of the acid is conducted at a reaction temperature of 30 to 200° C.

* * * * *